(12) United States Patent
Gubellini et al.

(10) Patent No.: US 9,179,923 B2
(45) Date of Patent: Nov. 10, 2015

(54) RIBBED SURGICAL BUR

(75) Inventors: Matteo Gubellini, Douglas (IE); Kevin Manley, Cobh (IE)

(73) Assignee: Stryker Ireland, Ltd., Carrigtwohill (IE)

( * ) Notice: Subject to any disclaimer, the term of this patent is extended or adjusted under 35 U.S.C. 154(b) by 672 days.

(21) Appl. No.: 13/402,993

(22) Filed: Feb. 23, 2012

(65) Prior Publication Data
US 2012/0150209 A1 Jun. 14, 2012

Related U.S. Application Data

(63) Continuation of application No. PCT/EP2010/005213, filed on Aug. 25, 2010.

(60) Provisional application No. 61/237,050, filed on Aug. 26, 2009.

(51) Int. Cl.
*A61B 17/32* (2006.01)
*A61B 17/16* (2006.01)
*B23C 5/10* (2006.01)
*A61C 3/02* (2006.01)

(52) U.S. Cl.
CPC .......... *A61B 17/1615* (2013.01); *B23C 5/1009* (2013.01); *A61B 17/1671* (2013.01); *A61B 17/1679* (2013.01); *A61B 17/1688* (2013.01); *A61C 3/02* (2013.01); *B23C 2210/086* (2013.01)

(58) Field of Classification Search
CPC .......... A61B 17/1613; A61B 17/1615; A61B 17/1671; A61B 17/1679; A61B 17/1688; A61B 17/32002; A61B 17/320758; B23C 5/1009; B23C 2210/086; A61C 3/02; B23B 51/00; B23B 2251/56; B23B 2251/14; B23B 2251/40; B23B 2251/241; B23B 2251/406; B23B 2251/52; B23D 77/003
USPC ............... 606/79, 80, 81, 110, 127, 128, 159, 606/167, 170, 180; 408/227–230
See application file for complete search history.

(56) References Cited

U.S. PATENT DOCUMENTS

| 5,759,185 A | 6/1998 | Grinberg |
| 5,888,200 A | 3/1999 | Walen |
| 6,562,055 B2 | 5/2003 | Walen |

(Continued)

FOREIGN PATENT DOCUMENTS

| JP | 06-061410 U | 8/1994 |
| JP | 2002-233910 A | 8/2002 |

(Continued)

OTHER PUBLICATIONS

EPO, "Int'l. Prelim. Exam Rpt. for PCT/EP2010/005213", Oct. 18, 2011.

(Continued)

*Primary Examiner* — Ryan Severson
*Assistant Examiner* — Rachel S Papeika (57) ABSTRACT

The bur includes a shaft to which a bur head is attached. The bur head includes a plurality of flutes. Each flute at least has a rake surface, a cam surface and a cutting edge. The rake surface extends radially outwardly from the longitudinal axis of the head. The rake surfaces define the flute cutting edge (38). The associated cam surface curves away from the rake surface. One or more ribs extend radially outwardly from the cam surface.

42 Claims, 10 Drawing Sheets

(56) References Cited

U.S. PATENT DOCUMENTS

| | | |
|---|---|---|
| 2005/0271482 A1 | 12/2005 | Volokh |
| 2008/0132929 A1 | 6/2008 | O'Sullivan et al. |
| 2008/0167653 A1 | 7/2008 | Watlington et al. |
| 2010/0063524 A1 | 3/2010 | McCombs |
| 2010/0121365 A1 | 5/2010 | O'Sullivan et al. |
| 2010/0209200 A1 | 8/2010 | Delacretaz |

FOREIGN PATENT DOCUMENTS

| | | |
|---|---|---|
| WO | 2007/010389 A1 | 1/2007 |
| WO | 2009/063261 A1 | 5/2009 |

OTHER PUBLICATIONS

Stryker, Print for Part No. 5820-607-030, Neuro Drill, Soft Touch, Dec. 2007.

RIBBED SURGICAL BUR

RELATIONSHIPS TO EARLIER FILED APPLICATIONS

This Application is a continuation of International Application No. PCT/EP2010/005213 filed 25 Aug. 2010 which designated the United States. The '213 PCT Application is a non-provisional application based on and that claims priority from U.S. Pat. App. No. 61/237,050 filed 26 Aug. 2009. The contents of the above-identified application are explicitly incorporated herein by reference.

FIELD OF THE INVENTION

The present invention relates generally to surgical burs. More specifically, the present invention relates to burs having a head with a geometry designed to reduce noise/vibration associated with applying the head to a surgical site to remove tissue.

BACKGROUND OF THE INVENTION

A cutting accessory is an implement that typically removably attached to a powered surgical handpiece to perform a surgical procedure. One cutting accessory used to perform a surgical procedure is a bur. A bur generally comprises a head formed from rigid material, typically metal, shaped to have a number of flutes. The flutes are formed to define cutting edges. The cutting edges are typically designed to cut hard tissue, such as bone or cartilage. A shaft extends proximally from the head. A proximal end of the shaft often has a feature that facilitates locking the shaft to the powered handpiece. Actuation of the handpiece results in rotation of the bur. During a surgical procedure, the head of the bur is placed against a surgical site where a section of tissue is to be removed. The rotating cutting edges excise tissue away from the surgical site. Burs of various shapes and sizes are used in procedures such as orthopedic surgery, neuro and spinal surgery, ear nose and throat surgery and in other surgical procedures to selectively remove a section of tissue.

Conventional burs work well for the general purpose of removing tissue. Nevertheless, a problem associated with some burs is excessive noise/vibration and possibly chatter. Chatter is the escalation of the noise/vibration of the bur to a resonance level. Chatter is often visualized as a relatively large spike or group of spikes in the amplitude of the noise/vibration experienced by a bur. Some prior art burs exhibit better characteristics than others with respect to noise/vibration and chatter. However, when noise/vibration and chatter are minimized, cutting efficiency is often reduced. One such bur is the subject of the Applicants' Assignee's U.S. Patent Pub. No. US 2008/0132929 A1/WO 2007/010389 A1, SURGICAL BUR WITH ANTI-CHATTER FLUTE GEOMETRY, which is explicitly incorporated herein by reference. When cutting efficiency is reduced, the head of the bur must make additional rotations to cut the same amount of material thereby generating more heat. Thus, there is a need in the art for a bur that reduces excessive noise/vibration while preventing undesirable heating of the head of the bur.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION OF THE INVENTION

Figure 1:
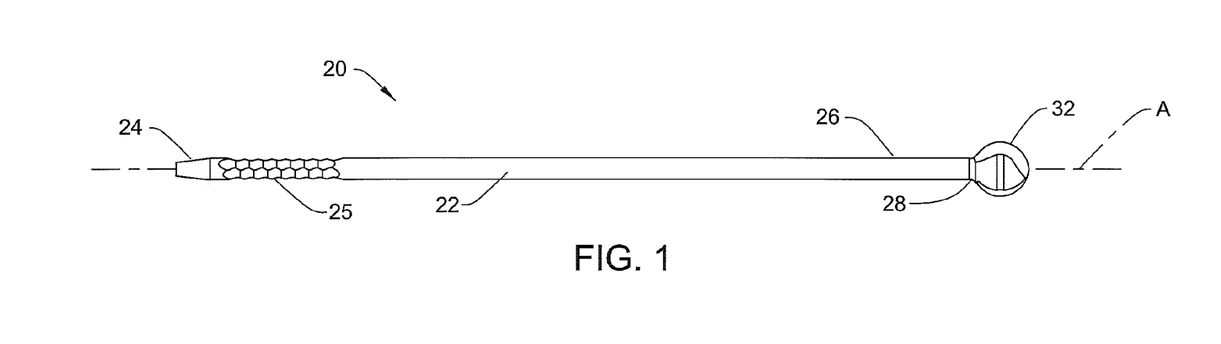
FIG. 1 is an elevational view of a surgical bur of the present invention.
Figure 2:
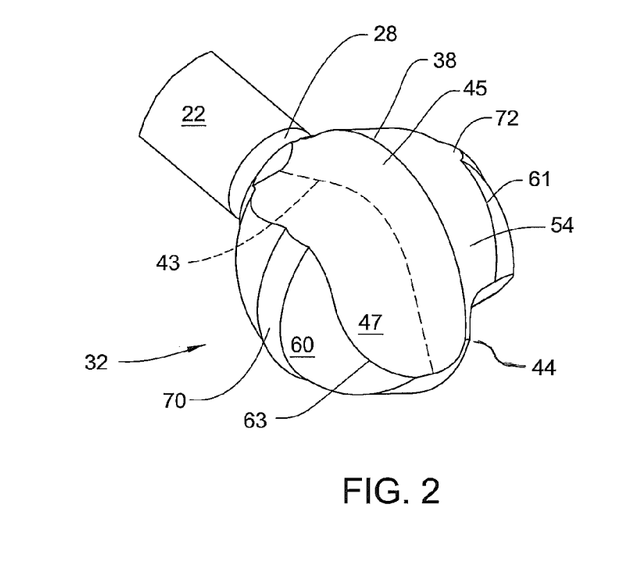
FIG. 2 is a perspective view of a head of the surgical bur of the present invention.
Figure 3:
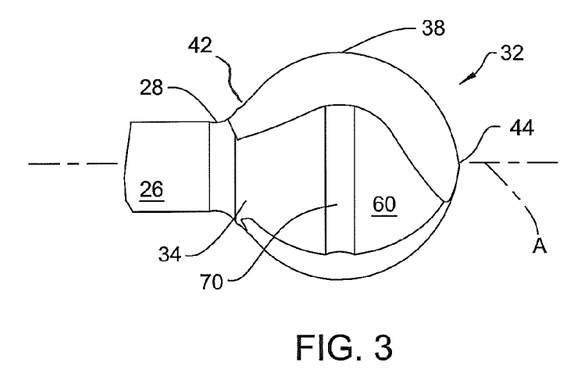
FIG. 3 is a front view of the head of the surgical bur.

Referring to the Figures, wherein like numerals indicate like or corresponding parts throughout the several views, a surgical bur 20 for removing or excising tissue from a surgical site is generally shown at 20 in FIG. 1. The bur 20 can be used for removing several types of tissue including cartilage and bone. The bur 20 can be used in surgical procedures such as orthopedic surgery, neurosurgery, spinal surgery, ear, nose and throat surgery and in other surgical procedures in which part of the procedure requires the removal or excision of tissue.

Referring to FIG. 1, the bur 20 includes a shaft 22 having a proximal end 24 and a distal end 26 ("distal" shall be understood to mean toward the surgical site to which the bur 20 is applied and "proximal" means away from the surgical site). The shaft 22 lies along a longitudinal axis A. A neck 28 of slightly smaller diameter than a main section 30 of the shaft 22 is provided at the distal end of the shaft 22. The proximal end 24 of the shaft 22 is provided with coupling features 25. The coupling features 25 are geometric features that facilitate the removable engagement of the bur 20 to a coupling assembly integral with a rotating shaft of a powered surgical tool (not shown) with which the bur 20 is used. The illustrated coupling features 25 are indentations described in U.S. patent application Ser. No. 12/205,103, filed 5 Sep. 2008, published as U.S. Pat. Pub. No. 2010/0063524 A1 (WO 2010/028001 A2), the contents of which are explicitly incorporated by reference. Alternative coupling features are shown in U.S. Pat. No. 5,888,200, issued Mar. 30, 1999, MULTI-PURPOSE SURGICAL TOOL SYSTEM, the contents of which are hereby incorporated by reference. Other alternative geometries for the coupling features are illustrated in U.S. Pat. No. 6,562,055, issued May 13, 2003, CUTTING ATTACHMENT FOR A SURGICAL HANDPIECE DESIGNED TO BE SELECTIVELY COUPLED TO THE HANDPIECE, the contents of which are hereby explicitly incorporated by reference. It should be appreciated that these coupling feature geometries are exemplary, not limiting. The geometry of the coupling features 25 is not intended to limit the present invention. For example, the smooth walled shaft itself may simply be held to the handpiece by chuck teeth that are part of the handpiece coupling assembly.

The incorporated by reference U.S. Pat. No. 5,888,200 also discloses one handpiece that can be used to actuate bur 20 of this invention.

A bur head 32 is disposed on the neck 28 of the shaft 22. Preferably, the head 32 is integrally formed with the shaft 22. In the embodiment of the invention illustrated in FIGS. 2-5, bur head 32 has a generally spherical shape and extends radially outwardly beyond the shaft 22. The head 32 includes a proximal end 34 fixed to the neck 28. The head 32 extends from the proximal end 34 to a distal end tip 36. The head 32 includes a plurality of cutting edges 38 configured to cut or excise tissue. In the embodiment shown, two cutting edges 38 are present (see FIG. 4). Each of the cutting edges 38 preferably extends in a generally arcuate shape from the proximal end 34 to a location slightly proximal to the distal end tip 36. An apex 40 of each of the cutting edges 38 is generally located midway between the proximal 34 and distal 36 ends of the head 32. Each of the cutting edges 38 have a proximal end 42 disposed at the proximal end 26 of the head 32. The proximal ends 42 of the cutting edges 38 are radially spaced away from the longitudinal axis A at a radius approximating the outer diameter of the distal end of the neck 28. Each of the cutting edges 38 extends from the distal end 26 of the shaft 22 to a tip edge 44.

Each cutting edge 38 is part of a flute 46. In the illustrated version of the invention bur head 32 is formed to have two flutes 46 that are symmetrically located around axis A and, since they are part of the bur head, extend radially extend radially beyond the shaft 22. Flutes 46 convey the excised material away from the cutting edges 38 during use.

Each of the flutes 46 is shaped to have four outer surfaces. One of these surfaces is the rake surface 45. Each rake surface 45 extends outwardly from the center of the bur head 32. Generally, each rake surface 45 is planar. In the illustrated version of the invention, each rake surface 45 is approximately crescent shaped. One end of the rake surface 45 is located adjacent the proximal end of the bur head 32. The opposed end of the rake surface 45 is at the distal end of the bur head 32. The rake surfaces 45 are not, however centered along the plane perpendicular to the longitudinal axis of the bur 20 that extends through the widest diameter section of the bur head 32. Instead, each rake surface is at its widest, the length between its inner and outer edges, along an axis that is forwarded of the widest plane through the bur head 32. This width axis across the rake surface 45 also forms an acute angle with the longitudinal axis of the bur 20 along an arc that extends toward the distal end of the bur head 32. The outer edge of each rake surface 45 is the cutting edge 38 of the flute 46 with which the rake surface is integral.

The second surface of each flute 46 is a relief surface 54. The flute relief surface 54 extends arcuately away from adjacent rake surface 45. Each flute cutting edge 38 is formed by the intersection of the rake surface 45 and the contiguous relief surface 54. As a result of some methods of manufacturing the bur of this invention, relief surface 54. Alternatively, as a result of other methods of manufacture, relief surface 54 is generally in the form of a slice section of the outer surface of a torus. In the illustrated version of the invention, each relief surface 54 extends from bur head distal end tip 36 to the bur head proximal end 34. Each flute cutting edge 38 thus extends the distance along the bur head 32 as the relief surface 54 with which the edge is integral.

Figure 4:
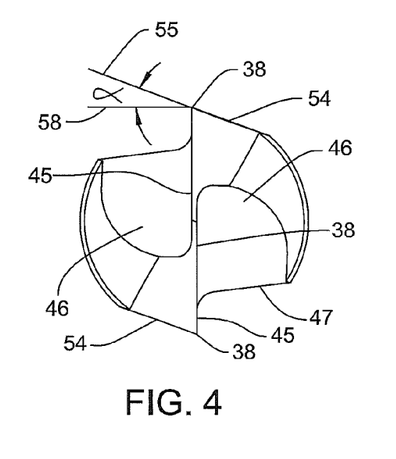
FIG. 4 is an end view of the head of the surgical bur.

The sharpness of the angle around the cutting edges 38 is a function of the angle between the rake surface 45 and the adjoining relief surface 54. Referring to FIG. 4, an angle $\alpha$ between a line 55 that extends from the relief surface 54 and a line 58 tangent to the cutting edge 38 is typically between 0 and 30°. Tangent line 58 is defined as a conventional tangent line of a circle with a radius equal to the radial dimension of the cutting edge 38. This angle $\alpha$ is sometimes referred to as the clearance angle or relief angle. Here it is assumed the rake angle is 0°. A rake angle is considered to be 0° when flute 46 is shaped so that as the rakes surface 45 rotates against tissue, the angle between the rake surface 45 and the tissue is 90°.

A cam surface 60 is the third surface of each flute 46. Each cam surface 60 extends between the trialing edge of the associated relief surface 54 (the surface arcuately spaced from the rake surface 45. Each cam surface 60 forms a first edge 61 with the intersecting relief surface 54. Each cam surface 54 terminates at a second edge 63 that is arcuately spaced from the first edge. Cam surfaces 60 are in form of slice sections of the outer surfaces of a sphere. Both the relief surfaces 54 and the cam surfaces 60 are centered on the center point internal to the bur head 32. In some versions of the invention, the radial distance of the relief surfaces 54 to this center point is greater than the radial distance of the cam surfaces 60 to this point. In the bur of FIGS. 2-5, the most distal end of each cam surface 60 is located proximal to the bur head distal end tip 36. The cam surfaces 60 extend to the proximal end of the bur head 32.

The arc subtended by each cam surface in the lateral plane, the plane perpendicular to the longitudinal axis through the bur head 32, varies along the length of the bur head. This arc is smallest at the most distal of the cam surface 60. Moving proximally along the bur head 32, the arc increases until the widest diameter section of the bur head. Proximal to the widest diameter portion of the bur head 32, the arc of the cam surface remains substantially constant along the remained of the length of the bur head 32.

The fourth surface integral with each flute 46 is a clearance surface 47. Each clearance surface 47 extends inwardly, towards the center of the bur head 32. At a location immediately outwardly of the bur head longitudinal axis, each clearance surface 47 curves and transitions into the rake surface 45 of the adjacent flute 46. Not identified is the curved transition surface between the rake surface 45 of one flute 46 and the clearance surface 47 of the adjacent flute. A phantom line 43 in FIG. 2 denotes the separation between these two surfaces 45 and 47. Along the length of the bur head 32, each clearance surface 47 starts along the lateral plane located proximal to the tip 36. Thus, as seen in FIG. 4, immediately proximal to tip 36 the opposed rake surfaces 45 overlap each other. The distal most portions of the relief surfaces 54 extend between the rake surfaces 45.

A rib 70 is disposed on each cam surface 60 and protrudes radially outwardly therefrom. Rib 70 has opposed leading and trailing ends 72 and 74, respectively. Rib leading end 72 is essentially an extension from the relief surface 54 contiguous with the cam surface 60 from which the rib 70 extends. Thus relative to a plane extending from the bur head longitudinal axis through the edge between the relief surface 54 and the cam surface 60, rib leading end 72 appears tapered. Rib trailing end 74 is located adjacent the clearance surface 47 adjacent the trailing edge of the cam surface 60 from which the rib 50. The rib trailing end 74 has a surface with the same curvature of the adjacent clearance surface 47.

In cross section, in a plane that extends each rib 70 appears to have a curved outer surface. Each rib has a crest 76 that defines the maximum radial dimension of the rib 70, relative to the bur head longitudinal axis.

Figure 5:
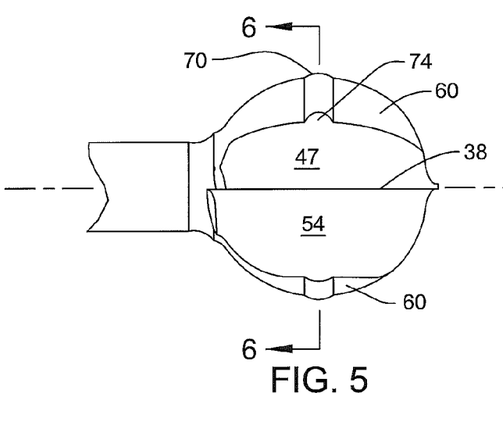
FIG. 5 is a top view of the head of the surgical bur.
Figure 6:
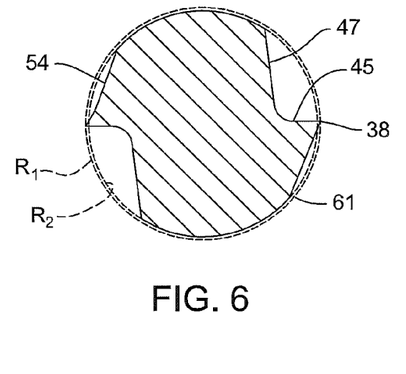
FIG. 6 is a cross-sectional view taken generally along the line 6-6 in FIG. 5 illustrating the radial dimension of a rib disposed on the head compared to a cutting edge of the head.

FIG. 6 illustrates a cross-section of the head 32 of the bur 20 taken along the line 6-6 in FIG. 5, which is through the crests 76 of the ribs 70. Radius $R_1$ is the radius of the cutting edges 38. Along the length of the bur head 32, this radius $R_1$, which is measured from Axis A, is greater than the radius of the coplanar portions of the cam surface 60, except where rib 70 is present, in FIG. 6, radius $R_2$. At the location along the length of the bur head 32 where the cutting edge 38 has its maximum diameter, radius $R_1$ is at a maximum, this radius is between 1 to 20% greater than and, often 6 to 10% greater than the radius $R_2$, the radius of cam surface 60 where rib 70 is not present. Extending along the length of the bur head 32, the absolute difference in length of these two radii, (Radius of Cutting Edge-Radius of Rib-Free Cam Surface), is generally constant. Thus, at locations proximal and distal to the maximum diameter of the cutting edges 38, the percent difference in radial distance of the cutting edges 38 in comparison to the ribless cam surfaces 60 increases from the above relative ranges.

At the locations along bur head 32, where ribs 70 are present, the rib crests 76 have a radius substantially equal to radius $R_1$ of FIG. 6. However, this is not a requirement for all versions of the invention. In some versions of the invention at locations where a rib 70 is present, the radius of the cutting edge and the radius of the crest of the rib can vary, plus or minus, by 6% or less.

Figure 7:
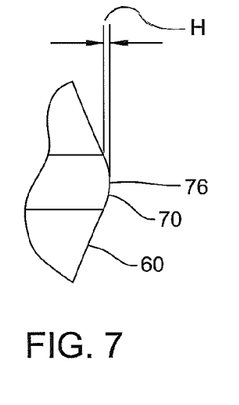
FIG. 7 is a close-up view of the rib.

FIG. 7 illustrates the height of a rib 70 above the cam surface 60 form which the rib extends. Here, $R_2$ is the radius of rib crest 76 relative to the bur head longitudinal axis. Assuming $R_1=R_2$, the ribs 70 are preferably raised from the cam surface 60 a predetermined height $H_1$ that is preferably between 1 and 20% of the radial length of the underlying cam surface.

The head 32 of the bur 20 may be formed by shaping the head 32 from a workpiece of material such as metal, including, but not limited to titanium, stainless steel, tool steel, tungsten carbide alloys, nickel-titanium alloys and the like. Grinding, electro-discharge machining, laser cutting or other machining methods may be employed to form the head 32 of the bur 20. The manner in which the head 32 of the bur 20 is formed is not intended to limit the invention.

Figure 8:
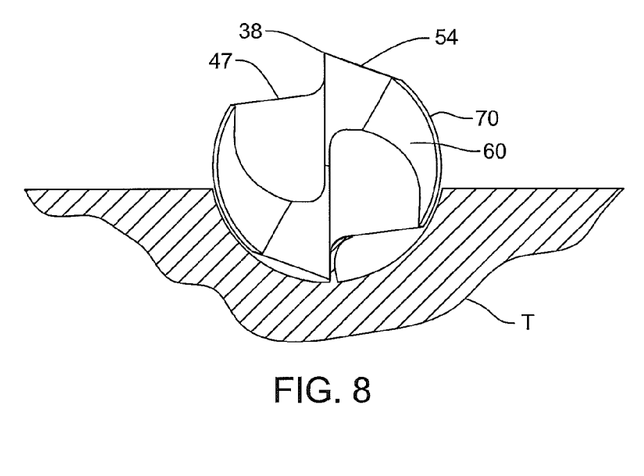
FIG. 8 is an end view of the head of the bur showing use in cutting tissue at a surgical site.

Operation of the bur 20 is shown in FIG. 8. During operation, the head 32 of the bur 20 rotates to excise tissue away from a surgical site S. Tissue T may be any form of tissue in the body, human or otherwise, such as cartilage and bone. Often the bur is rotated at speeds between 500 and 100,000 RPMs. As illustrated, as bur head 32 rotates (here counterclockwise), the cutting edges 38 penetrate into a layer L of the tissue T that then moves into the corresponding flute 46 of the head 32. When the bur head 32 is applied to the tissue T, three forces work against the bur head. A first one of these forces is the torque that rotates the bur head. The second force is the force $F_A$ the user imposes on the bur 20, actually the handpiece used to rotate the bur, so as to press the bur head against the tissue T. The third force is the reaction the tissue places on the bur head in opposition to the first two forces. The opposed and out of phase application of these forces against the bur head 32 when the head is pressed against tissue are what causes the unintended vibration of the bur.

Figure 8A:
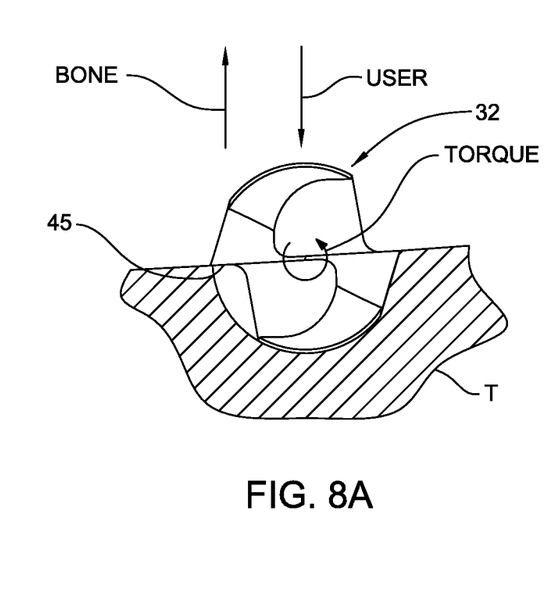
FIGS. 8A, 8B and 8C are cross sectional views that sequentially illustrate the rotation of the bur at the surgical site.

As the bur head rotates, a cutting edge of a flute 46 is rotated against the uncut tissue, FIG. 8A. The combination of the torque and user force causes the cutting edge to bear into the tissue. As a consequence of the rotation of the bur head, the rake surface 45 is pressed against the uncut tissue. The continued rotation of the bur head 32 causes the flute 46 to scrape away the tissue immediately in front of the rake surface 45. As the flute 46 continues to rotate, the relief surface 54 rotates into the space formed by the removal of the tissue. Owing to the angle between rake surface 45 and the relief surface 54, there is a clearance between the relief surface and the adjacent surface of the uncut tissue, seen in FIG. 8B. The presence of this clearance allows the force the user places on the bur head to push the flute deeper into the tissue.

Figure 8B:
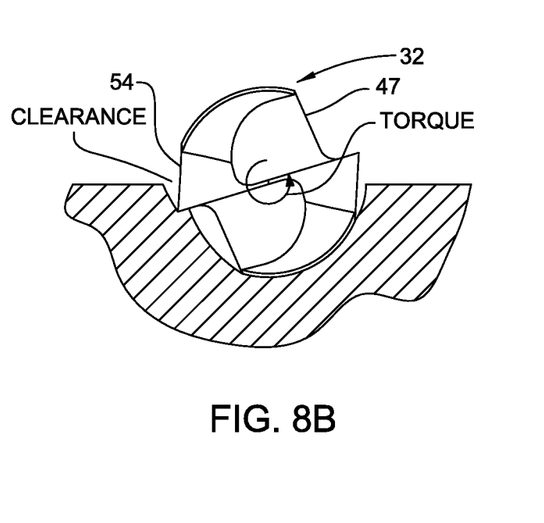

However, as a consequence of the presence of the clearance between bur head and the tissue, the opposed and out of phase forces that act against the bur head 32 causes the flute to repeatedly strike the uncut tissue. This repeated striking of the bur head 32 against the tissue is what is felt as bur vibration.

Figure 8C:
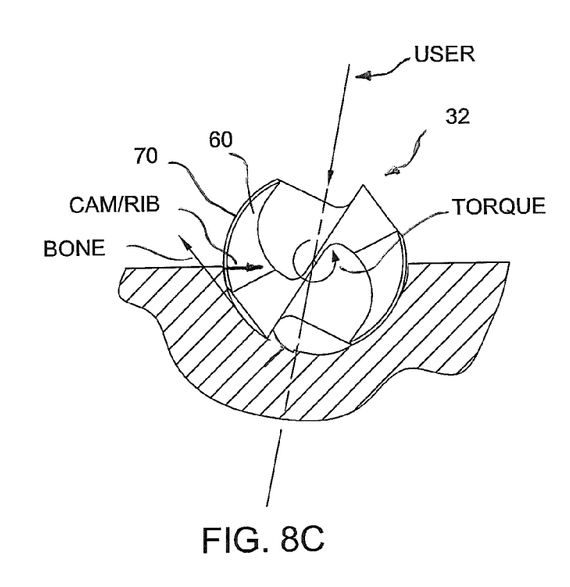
Figure 9:
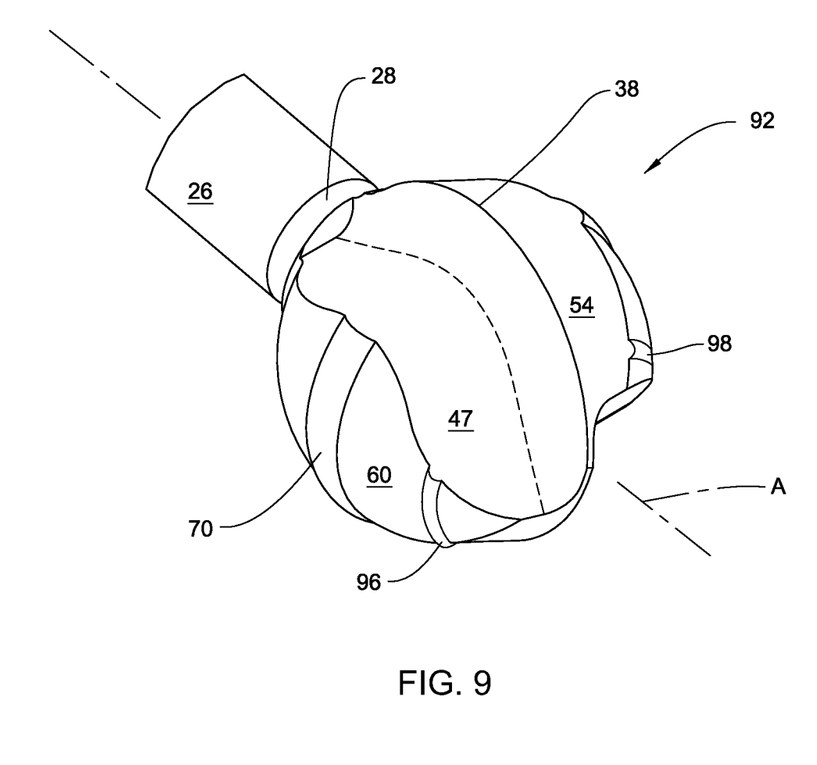
FIG. 9 is a perspective view of an alternative head of the surgical bur of the present invention.
Figure 10:
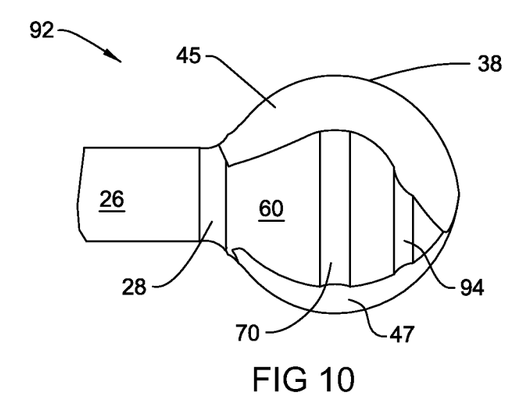
FIG. 10 is a side view of the bur of FIG. 9.
Figure 11:
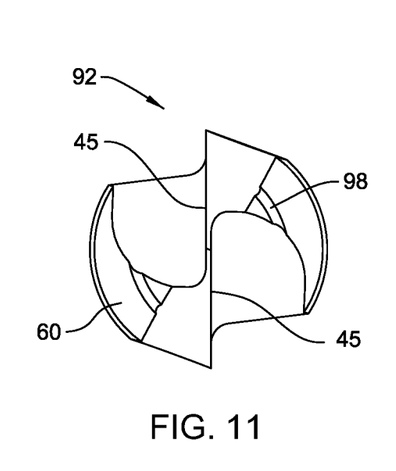
FIG. 11 is a distal end view of the bur of FIG. 9.
Figure 12:
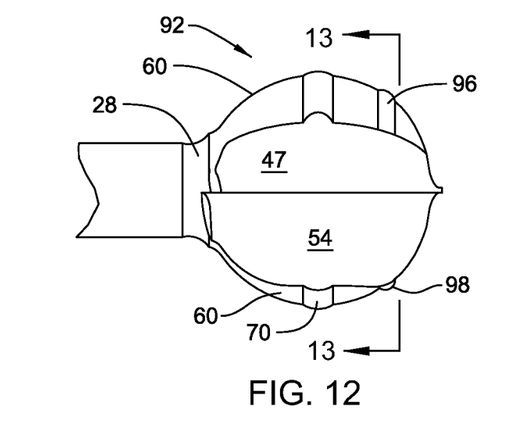
FIG. 12 is a second side plan view of the bur of FIG. 9.

As the flute relief surface 54 rotates away from the surface of the tissue being cut, the adjacent cam surface 60 rotates toward this tissue, FIG. 8C. If rib 70 is not present, the force the user places on the bur head would cause the cam surface to strike the tissue. The repetitive action of the cam surfaces 60 hitting the tissue followed by the cutting edges 38 digging into the tissue is believed an added source of back and forth vibration of the bur. However, in this invention, as the cam surface 60 rotates toward the tissue, the associated rib 70 is pressed against this tissue. This rib-against-tissue abutment reduces, if not eliminates, the extent to which each flute 46, after performing its cutting operation, is pressed against the tissue. The reduction of the extent to which each flute 46 is repetitively pressed against the tissue reduces the reaction of the tissue in opposition to this action. The cumulative effect of the reduction of this flute-against-tissue motion and subsequent forces imposed in opposition to this motion is the reduction in back and forth vibration of the bur 20. The reduction of this vibration results in a like reduction in what the practitioner using the bur 20 perceives as bur chatter.

Ribs 70 do more than reduce the flute-against-tissue contact that contributes to bur vibration. Each rib 70 holds the rest of the associated flute cam surface 60 away from the underlying tissue. This reduces the extent to which debris, cut tissue, disposed over the uncut tissue is pressed between the uncut tissue and the overlying flute 46. If these debris were simply compressed between the uncut tissue and the flute 46, the rotation of the flute would cause the friction heating of this tissue. This heating can be so great that it would essentially cause the debris to burn. This burning can potentially cause damage to the underlying uncut tissue.

This, either alone, or coupled with the cutting efficiency provided by the relief surfaces 54, the spacing provided by the ribs 70 helps ensure that when bur of this invention is used the tissue is subject to heating that typically does not cause damage. It has been shown in testing that during operation the head 32 of the bur 20 reaches a peak temperature of below 60° C. and often below 50° C., and even below 45° C.

Further if, instead of the rib being present, the radius of the cam surface was increased, the extent to which flute could be pressed into tissue so as to increase the aggressiveness of the cutting process would be limited. Instead, with the bur 20 of this invention, only around where the rib 70 is present does the presence of the rib limit the pressing in of the rest of the bur head against tissue. Thus, while the presence of the rib reduces vibration, it does not substantially eliminate the ability of the practitioner to use the bur of this invention to aggressively cut tissue.

Still another feature of bur 20 of this invention is that while rib 70 is present, the rib is spaced from the cutting edge by a distance equal to the maximum arch subtended by the relief surface 54. The spacing away of the rib 70 from the rake surface 45 means that the leading surface of the rib, which essentially would be an extension of the rake surface, does not present a cutting edge to the tissue that radially projects beyond the cutting edge defined by the interface between the rake surface 45 and the relief surface 54. This cutting edge, if present, could potentially overly aggressively cut into the tissue against which it is pressed.

Flutes 46 can be shaped so that the relief surfaces 54 can be modified to adjust the depth of cut. However, this is balanced with the noise/vibration caused by the bur 20. As the area of the relief surface 54 increases, so does the noise/vibration caused by the bur 20. Therefore, the bur 20 is preferably designed such that the noise/vibration does not escalate to an amplitude of vibration approaching resonance which would otherwise cause chatter in the bur 20. By utilizing the relief surfaces 54, cutting efficiency can be increased, i.e., relative to embodiments in which the relief surface 54 is not present, by reducing the number of rotations of the head 32 of the bur 20 needed to excise a desired volume of tissue.

As previously stated, in the embodiment of FIGS. 1-8c the rib 70 is axially disposed on the cam surface 60 at a position of maximum radial dimension of the cam surface 60. However, in other embodiments, the rib 70 can alternatively be positioned on the cam surface 60 at other longitudinal positions along the bur head 32 where the head radius is less than the maximum radius Likewise, as shown in FIGS. 9-13, a bur head 92 of this invention has flutes 94 with two ribs 70 and 96. Bur head 92 has substantially the same features as bur head 32. Each rib 70 is located at the same position on cam surface 60 as the corresponding rib 70 of bur head 32. Each rib 96 is extends outwardly from the cam surface 60 at a location distally forward of rib 70.

Figure 13:
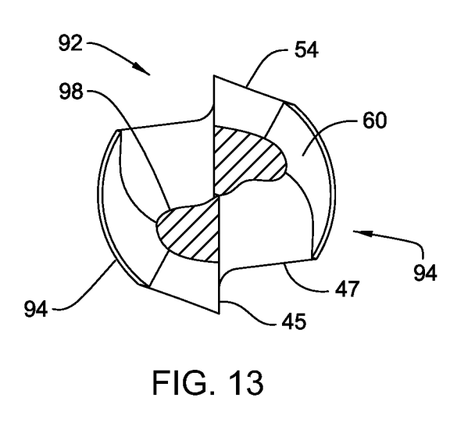
FIG. 13 is a cross-sectional view taken generally along the line 13-13 in FIG. 12 of the bur of FIG. 9.

FIG. 13 illustrates a cross-section of bur head 92 taken along the line 13-13 in FIG. 13. Again, it should be appreciated that, except where ribs 70 and 96 are present, the radius of cam surface 60 in lateral planes is less than the radial length of the corresponding cutting edge 38, distance $R_3$. As shown in FIG. 13, each of the crests 98 of the second ribs 96 are disposed a distance $R_4$ from the longitudinal axis A at this axial position on the head 32. As with the $R_1=R_2$ relationship between rib crest 76 and the coplanar cutting edge, $R_3=R_4$, rib crest 96 is an equal distance from axis A as the coplanar section of cutting edge 38.

In other embodiments, the rib or ribs may not be disposed entirely on a plane passing through the maximum radial dimension of the cam surfaces but may assume a spiral shape, a curved shape, or be formed of multiple spaced segments. Also, along the length of the rib, the height of the rib may vary.

Figure 14:
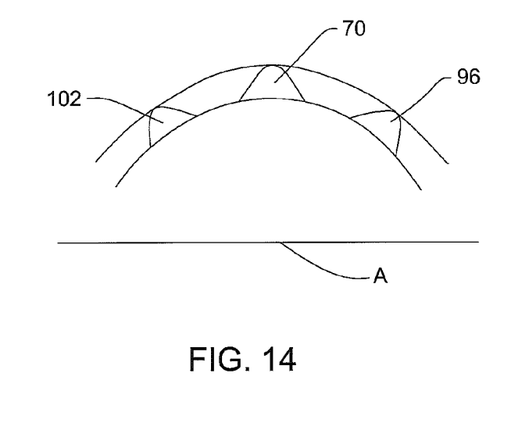
FIG. 14 illustrates a comparison of a radial dimension of one cutting edge to two ribs on a cam surface.

Also, as depicted in FIG. 14, shows another feature of a bur head of this invention. Here, the distance from the head longitudinal axis to the cam surface varies along the length of the axis. The relative heights of the longitudinally spaced apart ribs 70, 96 and 102 relative to the underlying cam surface is however constant. Here rib 102 is located proximal to rib 70, the rib located over the section of the cam surface 60 with the greatest length. While this relationship of relative rib height is preferred, it is not always required.

Figure 15:
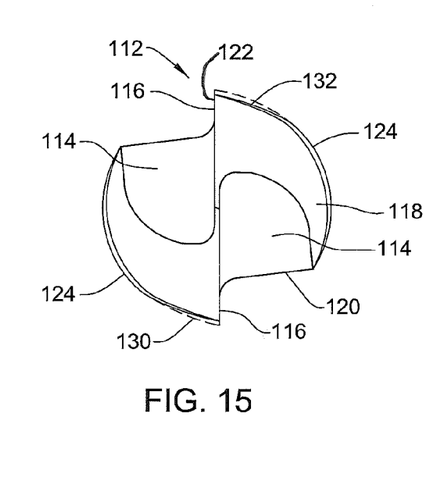
FIG. 15 is an end view of an alternative head of the surgical bur illustrating elimination of a relief surface.
Figure 16:
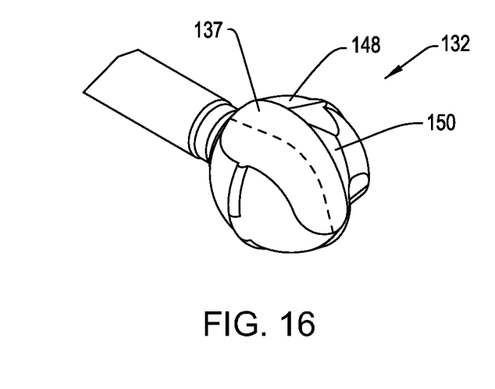
FIG. 16 is a perspective view of another alternative bur of this invention.
Figure 17:
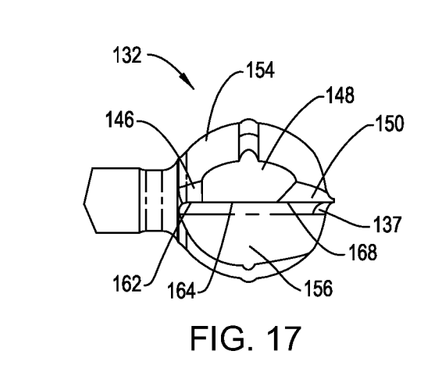
FIG. 17 is a plan view of a side of the view of the bur of FIG. 16.
Figure 18:
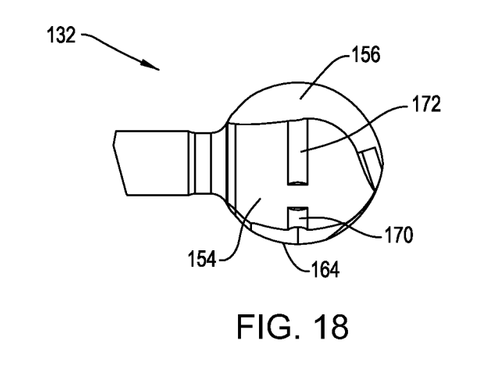
FIG. 18 is a second plan view of the bur of FIG. 16.
Figure 19:
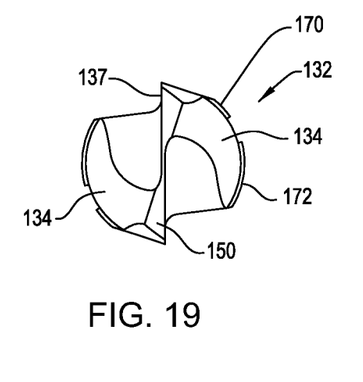
FIG. 19 is a plan view of the distal end of the bur of FIG. 16.

FIG. 15 illustrates in cross section an alternative bur head 112. In this version of the invention, there are two flutes 114. Each flute 114 has a rake surface 116, a cam surface 118 and a clearance surface 120. Each cam surface 118 extends arcuately away from the associated rake surface 116. The edge where each rake surface 116 and cam surface 118 meet is the flute cutting edge 122. There is no relief surface. A rib 124 extends radially over each cam surface 118. In the illustrated version of the invention, rib 124 extends from the cutting edge 122 to the edge between the cam surface 118 and the clearance surface 120. A bur head of this version of the invention may be fabricated so that, the end of the rib 124 adjacent the cutting edge 122 extends radially outwardly from the cutting edge 122. This is represented by phantom line 130 in FIG. 15. Line 130 represents the full heighted by rib 124 extending to the cutting edge.

Alternatively, as represented by solid line 132, bur head 112 can be formed so that adjacent that as the rib 124 extends around the cam surface 118 from the cutting edge 122 to towards the clearance surface 120, the height of the rib increases. In some embodiments of this version of the invention, the rib 124 may not be present, have no height relative to the cam surface 118, adjacent the cutting edge.

FIGS. 16-19 illustrate another alternative bur head 132 of this invention. Bur head 132 has two flutes 134 that are symmetric around the longitudinal axis of the head. Each flute 134 has a rake surface 137 similar to rake surface 45. A relief surface 148 extends angularly away the outer edge of rake surface 137. A cam surface 154 having the shape of slice through the outer surface of a sphere extends angularly away from the relief surfaces 148. Each flute 134 further has a clearance surface 156. Each clearance surface 156 extends inward from the trailing end of the associated cam surface 154, the end opposite the relief surface 152. The clearance surface 156 extends inwardly and curves into the inner portion of the rake surface 137 of the adjacent flute 134.

Relief surfaces 148 of bur head 132, unlike relief surface 54 of bur head 32, do not extend the full length of bur head 132. Instead, bur head 132 is formed so that each relief surface 148 extends forward from a location distally forward of the proximal end of the bur head and terminates at a location rearward of the proximal tip of the bur head. A proximal leading surface 146 is located immediately proximal to relief surface 148. A distal leading surface 150 is located immediately distal to relief surface 148. The leading surfaces 146 and 152 thus extend between rake surface 138 and cam surface 154. In planes perpendicular to the longitudinal axis of the bur head 132, the leading surfaces 146 and 150 form angles through the flute 134 with the adjacent rake surface 137 that are greater than the angles through the flute between the rake surface 137 and the relief surface 148. Thus, in this version of the invention, the flute cutting edge actually consists of three contiguous cutting edges; the edge 162 defined by rake surface 137 and leading surface 146; the cutting edge 164 defined by the rake surface and relief surface 148; and the cutting edge 166 defined by rake surface and leading surface 150. It should be appreciated that cutting edge 164 is the primary cutting edge. Cutting edges 162 and 166 are secondary cutting edges.

Leading surfaces 146 and 150 are present as a result of the method of manufacturing the bur of this invention. More particularly, leading surfaces 146 and 150 appear as a consequence of a grinding process that defines the cam surfaces 154 and the below described ribs 170 and 172. In some versions of this invention, lengthwise along the bur head 132, leading surface 146 extends over approximately 10 to 20% of the flute; relief surface 148 extends over 40 to 60% of the flute; and leading surface 142 extends over 30 to 40% of the flute. Typically of the three surfaces 146, 148 and 150, relief surface 148 is the longest when measured along an axis parallel to the longitudinal axis of the bur head 132.

If leading surfaces 146 and 150 were not present, cam surface 154 would extend to the rake surface 138 on the opposed sides of relief surface 148. In this version of the invention, the interfaces between the rake surface and the cam surface on the opposed sides of the relief surface would be the secondary cutting edges of the flute.

Bur head 132 is formed so that there are on each cam surface 154 there are two co-linear arcuately spaced apart ribs 170 and 172. In the illustrated version of the invention, ribs 170 and 172 project outwardly from the widest diameter section of the bur head 132. Rib 170 extends arcuately from the edge between relief surface 150 and cam surface 154. Rib 172 is arcuately spaced from rib surface 170 by an angle of between 10 and 30° and more often by an angle between 15 and 25°. Rib 172 extends to the interface between the cam surface 154 and the associated clearance surface 156.

Bur 132 of this invention has proven to be a surgical cutting tool that, using a grinding process can be manufactured relatively efficiently and with a high degree of consistency.

Alternative embodiments of other features of the invention are also possible. For instance, the features of the different versions of this invention may be combined.

Figure 20A:
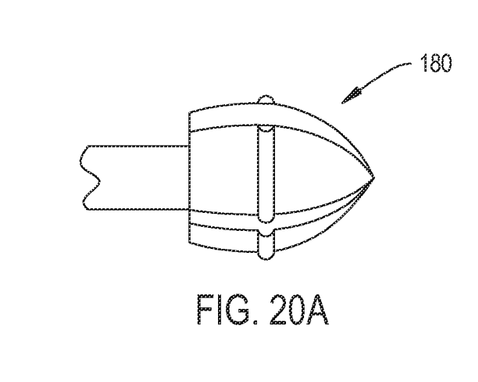
FIGS. 20A-20F are, respectively, side plane views of acorn head, barrel head, bullet head, egg, pear and drum shaped burs of this invention.
Figure 20B:
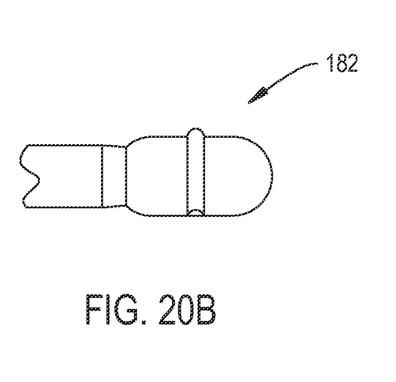
Figure 20C:
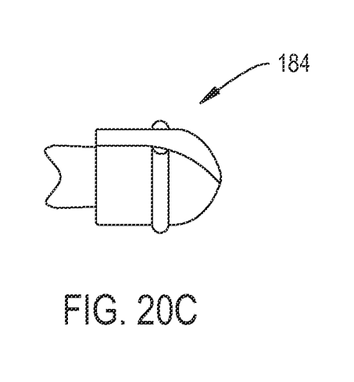
Figure 20D:
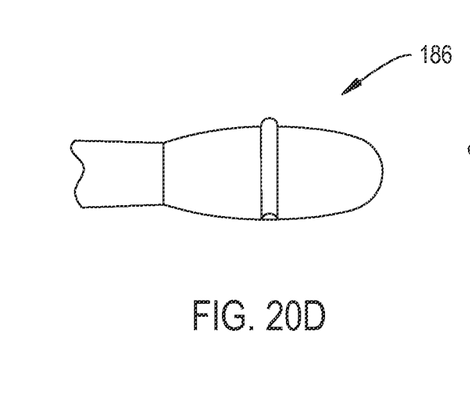
Figures 20E, 20F:
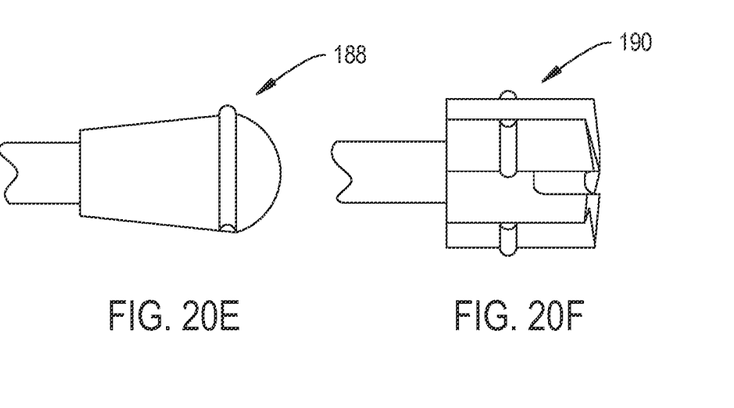

Likewise the disclosed spherical shaped bur heads are exemplary, not limiting. In alternative embodiments, the head 32 may have alternative shapes including acorn head 180 (FIG. 20A), barrel head 182 (FIG. 20B), bullet head 184 (FIG. 20C), egg head 186 (FIG. 20D), pear head 188 (FIG. 20E) or drum shaped 190 (FIG. 20F). In these alternatives, the rib or ribs disposed on the heads provide support for the heads at the surgical site to reduce noise/vibration.

Similarly there is no requirement that all versions of the invention have just two flutes. Versions of the invention with three of more flutes are possible. Likewise, there is no requirement that in all versions of the invention each flute have a cam surface from which a rib extends. Thus in a version of the invention with four flutes, only one pair of flutes may have cam surfaces. Generally though the cams should be arranged to minimize asymmetric loading of the bur. Likewise, there is no requirement that the flutes all be equagularly spaced apart from each other. Thus in some versions of the invention, the flutes may be asymmetrically arranged around the longitudinal axis of the bur head. Still for many versions of the invention a two flutes bur with the burs being symmetric around the longitudinal axis is the preferred version of the invention.

Similarly, there is no requirement that in all versions of the invention have a clearance surface that is distinct from the cam surface. In these versions of the invention, the cam surface, when viewed in cross section, has a spiral shape. Extending radially from the cutting edge with which the cam surface is integral, the cam surface extends both radially around the bur head longitudinal axis and inwardly toward this axis. The inner section of the cam surface terminates at or near the rake surface of the adjacent following flute.

In the above or any other version of the invention, the rib may not extend the full radial length around the cam surface with which the rib is integral. This would especially be true in versions of the invention wherein the rake surface-cam surface interface forms the flute cutting edge. In these versions of the invention, for the reasons set forth above, it is often preferable to form the bur head so that the rib is arcuately spaced away from the cutting edge.

In versions of the invention, where there is arcuate gap between adjacent collinear ribs there may be another rib that is along the length of the bur head, longitudinally spaced from the collinear ribs. This design ensures that the cam surface stays held off from the underlying tissue when the gap between the collinear ribs is located adjacent the tissue.

Similarly there is no requirement that in all versions of the invention, the ribs extend radially in a plane or planes perpendicular to the longitudinal axis of the bur head. In some versions of the invention, each cam surface may have one or more rib that is in a plane not at a 90° angle to the longitudinal axis of the bur head. Further, in some versions of the invention, the rib may not necessarily be a linear structure. A rib may be formed with bends such that on rib has different sections that are angled relative to each other.

The geometry of the transition surface, if any between each clearance surface and the rake surface of the adjacent flute may vary. In some versions of the invention a planar transition surface may be located between these two surfaces. In some versions of the invention, there may not even be a transition surface; these two surfaces may simply meet at an angle.

Similarly, in some versions of the invention, portions of the relief surface may be small radial distances from the longitudinal axis of the bur head than the adjacent cam surface. Further, depending of the method of manufacture, the relief surface may have a geometry that approaches that of a slice section through a sphere.

It is likewise understood that the shaft 22 of the bur 20 is not limited to that disclosed. The bur 20 may have a solid cylindrical shaft, as shown, or the bur may be tubular defining a hollow lumen (not shown) through which irrigating fluid is discharged or through which suction is drawn. In these embodiments, the shaft typically has an opening immediately proximal to the head of the bur. The opening functions as a port for accessing the lumen to either discharge irrigating fluid or to draw out materials by suction. In these embodiments, the coupling feature at the proximal end of the shaft is often a hub attached to the proximal open end of the shaft. The hub has both geometric features that facilitate the coupling of the bur to a handpiece and a port to establish fluid communication to a suction device or from a source of irrigating fluid.

Likewise, there is no requirement that in all versions of the invention the neck between the bur shaft 30 and head 32 be of smaller diameter than the shaft. In the described version of the invention, this feature is present for manufacturing reasons. In some versions of the invention, this neck may be absent or have a diameter larger than that of the adjacent shaft.

Similarly, in some versions of the invention the "geometric feature" integral with the proximal end of the shaft 22 for coupling the shaft to the handpiece may simply be that that portion of the shaft has a certain outer diameter. The geometric feature is thus a portion of the smooth walled shaft 22.

Obviously many modifications and variations of the present invention are possible in light of the above description. While this description is directed to particular embodiments, it is understood that those skilled in the art may conceive of modifications and/or variations to the specific embodiments shown and described herein. Any such modifications or variations, which fall within the purview of this description, are intended to be included herein as well. It is understood that the description herein is intended to be illustrative only and is not intended to be limited.

What is claimed is:

1. A surgical bur for removing or excising tissue from a surgical site, said surgical bur including:
   an elongated shaft having opposed proximal and distal ends, the proximal end of the shaft shaped for coupling to a surgical tool capable of rotating the shaft; and
   a bur head attached to the distal end of the shaft, the bur head having: opposed proximal and distal ends, the proximal end of said bur head being adjacent the distal end of said shaft; a longitudinal axis that extends between the ends; and a plurality of flutes, each flute having:
    a rake surface that extends outwardly from the longitudinal axis of the bur head and having an outer end that defines a flute cutting edge wherein, in lateral planes perpendicular to the longitudinal axis of the bur head, the flute cutting edge is located a first radial distance from the longitudinal axis of the bur head; and
    a cam surface that extends arcuately away from flute cutting edge towards an adjacent flute wherein, in the lateral planes perpendicular to the longitudinal axis of the bur head, the cam surface is located a second radial distance from the longitudinal axis of the of the bur head such that in a common lateral plane, second radial distance is less than the first radial distance
    wherein, at least one said flute is further formed to have at least one rib that extends outwardly from the cam surface and extends arcuately over a portion of the cam surface, wherein said at least one said rib, in cross section in a plane intersecting the bur head longitudinal axis: extends outwardly and proximally away from the cam surface to a crest, the crest being the portion of said rib that is spaced radially furthest from the bur head longitudinal axis; and, proximally from the crest, extends inwardly back to the cam surface so that said rib extends radially outwardly from sections of the cam surface located both distal to and proximal to said rib.

2. The surgical bur of claim 1, wherein said at least one flute is further shaped so that where said at least one rib is present, said crest of said rib is located a third distance from the bur head longitudinal axis, the third distance being greater than the second distance.

3. The surgical bur of claim 1, wherein:
    the bur head has a diameter that varies along the length of the bur head; and
    said at least one flute is formed so that said rib extends outwardly from the cam surface at a location wherein the bur head has a maximum diameter.

4. The surgical bur of claim 1, wherein said at least one flute is formed with plural ribs.

5. The surgical bur of claim 4, wherein said plural ribs are longitudinally spaced apart from each other on the cam surface.

6. The surgical bur of claim 4, wherein said plural ribs are arcuately spaced apart from each other.

7. The surgical bur of claim 1, wherein said at least one flute is further formed so that said rib has a leading end that is arcuately spaced away from the flute cutting edge.

8. The surgical bur of claim 1, wherein:
    said at least one flute is further formed to have a relief surface that extends away from the rake surface to the cam surface, the rake surface and the relief surface having an interface that forms the flute cutting edge; and
    said at least one rib has a leading end that extends arcuately around said cam surface from an interface between the relief surface and the cam surface.

9. The surgical bur of claim 8, wherein said relief surface extends the length of the bur head.

10. The surgical bur of claim 8, wherein said relief surface extends forward from a location distally forward from the bur head proximal end.

11. The surgical bur of claim 8, wherein said relief surface extends rearward from a location proximally rearward of the bur head distal end.

12. The surgical bur of claim 1, wherein each said flute further includes a clearance surface that extends inwardly from the end of the cam surface spaced from the cutting edge, each said clearance surface extending to the rake surface of an adjacent flute.

13. The surgical bur of claim 12, wherein said at least one flute with a rib is formed so that the rib extends over the cam surface to the clearance surface.

14. The surgical bur of claim 1, wherein the bur head has a shape of one selected from the group including: spherical; acorn head; barrel head, bullet head, egg, pear; and drum shaped.

15. The surgical bur or claim 1, wherein the shaft is formed with indentations that are engaged by the surgical tool to which the bur is coupled.

16. The surgical bur of claim 1, further including a neck located between the shaft and the bur head, the neck having a diameter less than the diameter of the shaft and greater than the adjacent portion of the bur head to which the neck is attached.

17. The surgical bur of claim 1, wherein at least a portion of each cam surface abuts the associated rake surface so as to define at least a portion of the flute cutting edge of the flute with which the rake surface and cam surface are integral.

18. The surgical bur of claim 1, wherein the bur head has two flutes and each said flute has at least one said rib.

19. The surgical bur of claim 1, wherein the bur head is formed so that the flutes are symmetrically arranged around the bur head longitudinal axis and each said flute has at least one said rib.

20. The surgical bur of claim 1, wherein said at least one rib is located proximally rearward from the distal end of the bur head.

21. The surgical bur of claim 1, wherein said at least one rib is located distally forward of the bur head proximal end.

22. The surgical bur of claim 1, wherein said at least one rib is formed to have a curved outer surface so that, as said rib extends distally from a proximal section of the cam surface, the outer surface of said rib curves distally and radially outwardly from the cam surface to the crest and, as said rib extends distally forward from the crest, the outer surface of said rib curves distally forward and radially inwardly to intersect a portion of the cam surface distal to said rib.

23. The surgical bur of claim 21, wherein the bur head, including said flutes, extend radially outwardly of said shaft.

24. The surgical bur of claim 1, wherein:
    at least a portion of the cam surface of said flute from which said at least one rib extends abuts the associated rake surface so as to define at least a portion of the flute cutting edge of the flute with which the rake surface and cam surface are integral; and
    said at least one rib extends radially outwardly from the portion of the cam surface that abuts the associated rake surface.

25. A surgical bur for removing or excising tissue from a surgical site, said surgical bur including:
    an elongated shaft having opposed proximal and distal ends, the proximal end of the shaft shaped for coupling to a surgical tool capable of rotating the shaft;
    a bur head attached to the distal end of the shaft, the bur head having:
        opposed proximal and distal ends, the proximal end of the bur head being adjacent the distal end of said shaft;
        a longitudinal axis that extends between the ends:
        a plurality of flutes, each flute having:

a rake surface that extends outwardly from the longitudinal axis of the bur head and having an outer end that defines a flute cutting edge; and a cam surface that extends arcuately away from the flute cutting edge, said flute being formed so that, in a common lateral plane perpendicular to the bur head longitudinal axis, at least a portion of the cam surface is located radially inward from the cutting edge relative to the bur head longitudinal axis; and at least one rib, said rib being disposed over the portion of the cam surface of at least one said flute, said at least one rib shaped so that, in cross section in a plane intersecting the bur head longitudinal axis, said at least one rib, extends outwardly and distally away from the cam surface to a crest, the crest being the portion of said rib that is spaced radially furthest from the bur head longitudinal axis; and, distally from the crest, inwardly back to the cam surface so that said rib extends radially outwardly from sections of the cam surface located both proximal and distal to said rib.

26. The surgical bur of claim 25, wherein:

the bur head has a diameter that varies along the length of the bur head; and said at least one flute is formed so that said rib extends outwardly from the cam surface at a location wherein the bur head has a maximum diameter.

27. The surgical bur of claim 25, wherein said at least one flute is formed with plural said ribs, said ribs being located over different sections of the cam surface.

28. The surgical bur of claim 25, wherein on said at least one flute from which said at least one rib extends, said rib is formed to have a leading end that is arcuately spaced away from the flute cutting edge.

29. The surgical bur of claim 25, wherein:

said at least one flute from which said at least one rib extends is further formed to have a relief surface that extends away from the rake surface to the cam surface, the rake surface and the relief surface having an interface that forms the flute cutting edge; and said at least one rib has a leading end that extends arcuately around said cam surface from an interface between the relief surface and the cam surface.

30. The surgical bur of claim 29, wherein said relief surface extends the length of the bur head.

31. The surgical bur of claim 25, wherein each said flute further includes a clearance surface that extends inwardly from the end of the cam surface spaced from the cutting edge, each said clearance surface extending to the rake surface of an adjacent flute.

32. The surgical bur of claim 31, wherein said at least one flute from which said at least one rib extends is formed so that said rib extends over the cam surface to the clearance surface.

33. The surgical bur of claim 25, wherein the bur head has a shape of one selected from the group including: spherical; acorn head; barrel head, bullet head, egg, pear; and drum shaped.

34. The surgical bur or claim 25, wherein the shaft is formed with indentations that are engaged by the surgical tool to which the bur is coupled.

35. The surgical bur of claim 25, wherein at least a portion each cam surface abuts the associated rake surface so as to define at least a portion of the flute cutting edge of the flute with which the rake surface and cam surface are integral.

36. The surgical bur of claim 25, wherein the bur head has two said flutes and each said flute has at least one said rib that extends outwardly from a portion of the cam surface of said flute that, in a common lateral plane, is located radially inwardly from the cutting edge of said flute.

37. The surgical bur of claim 25, wherein the bur head is formed so that each said flute has at least one said rib that extends outwardly from a portion of the cam surface of said flute that, in a common lateral plane, is located radially inwardly from the cutting edge of said flute.

38. The surgical bur of claim 25, wherein said at least one rib is located proximally rearward from the distal end of the bur head.

39. The surgical bur of claim 25, wherein said at least one rib is located distally forward of the bur head proximal end.

40. The surgical bur of claim 25, wherein said at least one rib is formed to have a curved outer surface so that, as said rib extends distally from a proximal section of the cam surface, the outer surface of said rib curves distally and radially outwardly from the cam surface to the crest and, as said rib extends distally forward from the crest, the outer surface of said rib curves distally forward and radially inwardly to intersect a portion of the cam surface distal to the rib.

41. The surgical bur of claim 25, wherein the bur head, including said flutes, extend radially outwardly of said shaft.

42. The surgical bur of claim 25, wherein: at least a portion of the cam surface of said flute from which said at least one rib extends abuts the associated rake surface so as to define at least a portion of the flute cutting edge of the flute with which the rake surface and cam surface are integral; and said at least one rib extends radially outwardly from the portion of the cam surface that abuts the associated rake surface.

* * * * *